United States Patent [19]

Kwan

[11] Patent Number: 5,200,558
[45] Date of Patent: Apr. 6, 1993

[54] S(+)-IBUPROFEN-L-AMINO ACID AND S(+)-IBUPROFEN-D-AMINO ACID AS ONSET-HASTENED ENHANCED ANALGESICS

[75] Inventor: King C. Kwan, Blue Bell, Pa.

[73] Assignee: Merck & Co., Inc., Rahway, N.J.

[21] Appl. No.: 743,545

[22] Filed: Aug. 9, 1991

Related U.S. Application Data

[63] Continuation of Ser. No. 422,466, Oct. 17, 1989, abandoned.

[51] Int. Cl.$^5$ ............................................. C07C 53/134
[52] U.S. Cl. ....................................... 562/496; 514/570
[58] Field of Search ......................... 562/496; 514/570

[56] References Cited

U.S. PATENT DOCUMENTS

| | | | |
|---|---|---|---|
| 4,279,926 | 7/1981 | Bruzzese et al. | 424/316 |
| 4,851,444 | 7/1989 | Sunshine et al. | 514/570 |
| 4,877,620 | 10/1989 | Loew et al. | 424/451 |

FOREIGN PATENT DOCUMENTS

| | | |
|---|---|---|
| 3638414 | 5/1987 | Fed. Rep. of Germany . |
| 093718 | 4/1988 | Japan . |

OTHER PUBLICATIONS

CA 111 (16): 140370f, 1989.
Biochemical Pharmacology, 35, No. 19, Oct. 1986, pp. 3403—3405.
Current Medical Research & Opinion, 3, No. 8, 1975, p. 552.
J. Pharm. Pharmacol., 28, 1976, pp. 256–257.
J. Pharm. Sciences, 56, 1967, p. 1686.
Biochem. & Biophys. Res. Comm., 61, No. 3, 1974, pp. 833–837.
J. Pharm. Pharmacol., 35, 1983, pp. 693–704.
Clin. Pharmacokinetics, 9, 1984, pp. 371–373.
J. Pharm. & Exp. Therapeutics, 232, No. 3, 1985, pp. 636–643.
Clin. Pharm. & Therapeutics, 41, No. 2, Feb. 1987, p. 200.
Clin. Pharm. & Therapeutics, 40, No. 1, 1986, pp. 1–7.
Chem. Abstracts, 106, 1987, No. 66922r.
Agents & Actions, 27, 455, 1989.
Biochem. Pharm., 37, 105, 1988.

*Primary Examiner*—Paul J. Killos
*Attorney, Agent, or Firm*—Charles M. Caruso; Melvin Winokur

[57] ABSTRACT

S(+)-ibuprofen-L-amino acids and S(+)-ibuprofen-D-amino acids, substantially free of other ibuprofen-amino acid stereoisomers, give an onset-hastened, enhanced analgesic response in humans.

23 Claims, No Drawings

S(+)-IBUPROFEN-L-AMINO ACID AND S(+)-IBUPROFEN-D-AMINO ACID AS ONSET-HASTENED ENHANCED ANALGESICS

This is a continuation of application Ser. No. 07/422,466, filed Oct. 17, 1989, now abandoned.

BACKGROUND OF THE INVENTION

Ibuprofen (I) is a well-known nonsteroidal antiinflammatory drug which possesses analgesic and antipyretic activity.

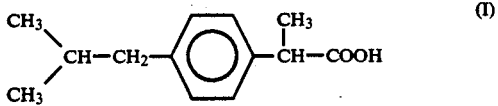

Ibuprofen has been marketed as a racemic mixture of the S(+) and R(−) enantiomers; however, recently there have been suggestions in the literature regarding an increased pharmaceutical benefit for S(+)-ibuprofen relative to the racemic mixture, see, for example, A. Sunshine et al U.S. Pat. No. 4,851,444, D. Lowe et al EPO publication 267,321, K. Williams et al Brit.J. of Pharm. 35 3404 (1986).

Ibuprofen as a carboxylic acid can form salts with bases, such as basic amino acids, examples of which are lysine and arginine. The low solubility of the acid form of ibuprofen is overcome by the use of the lysinate salt of ibuprofen. U.S. Pat. No. 4,279,926 describes the use of the lysine salt of Ibuprofen in relieving pain and inflammatory conditions in warm-blooded animals. However, there is no description in the literature of the compound S(+)-ibuprofen-L-lysine, i.e. the L-lysinate salt of S(+)-ibuprofen, or other L-amino acid salts of S(+)-ibuprofen; there is also no description of S(+)-ibuprofen-D-lysine or other D-amino acid salts of S(+)-ibuprofen.

DETAILED DESCRIPTION OF THE INVENTION

This invention relates to basic L-amino acid and D-amino acid salts of S(+)-ibuprofen. Such basic L-amino acids and D-amino acids include but are not limited to L-lysine, L-arginine, L-histidine and D-lysine, D-arginine and D-histidine. One embodiment of this invention is the L-lysine and L-arginine salts of S(+)-ibuprofen. A second embodiment is the D-lysine and D-arginine salts of S(+)-ibuprofen.

Where particular stereoisomeric forms are described in this invention, they are meant to be substantially free of any other stereoisomeric configuration. Substantially free should be taken to mean that the active ingredient contains at least 90% by weight of the desired stereoisomer and 10% or less of other stereoisomers. Preferably the weight % ratio is better than 95:5 and most preferably 99:1 or better. For example, S(+)-ibuprofen-L-lysine contains at least 90% by weight of this stereoisomer and 10% or less of other configurations of Ibuprofen-Lysine.

S(+)-ibuprofen-L-amino acid and S(+)-ibuprofen-D-amino acid exhibit an onset-hastened, enhanced analgesic response of longer duration compared to ibuprofen. Specifically, applicants have found that in humans S(+)-ibuprofen-L-lysine has a faster onset of analgesic action, an enhanced analgesic response and a longer duration of action than the same dose of racemic ibuprofen in the acid form or as racemic ibuprofen lysinate. S(+)-ibuprofen-L-lysine also exhibits a more rapid onset and an enhanced response of longer duration when compared to S(+)-ibuprofen. S(+)-ibuprofen-D-lysine produces similar results.

The employment of a particular basic amino acid stereoisomeric salt of ibuprofen which contains only one enantiomeric form of the acid and one enantiomeric form of the basic amino acid avoids introducing into the human body enantiomeric forms which are less therapeutically effective, may be toxic and which may put an unnecessary burden on the metabolic systems.

A third embodiment of this invention is a pharmaceutical composition for treating pain and inflammation in a human subject in need of such treatment, said composition comprising an onset-hastening, enhancing analgesically, effective amount of S(+)-ibuprofen-L-amino acid or S(+)-ibuprofen-D-amino acid and a non-toxic pharmaceutically acceptable carrier.

A further embodiment is the method of treating pain and inflammation in a human subject in need of such treatment comprising administering to such subject an onset-hastening, enhancing analgesically, effective amount of S(+)-ibuprofen-L-amino acid, or S(+)-ibuprofen-D-amino acid.

The amount of S(+)-ibuprofen-L-amino acid or S(+)-ibuprofen-D-amino acid to be administered will vary depending on the extent of the pain and/or inflammation and the tolerance of the patient. Typically the amounts will vary from 50 mg to 800 mg (amounts measured in mg ibuprofen). Preferred doses are 50, 100, 200, 300, 400, 600 and 800 mg.

Compositions of S(+)-ibuprofen-L-amino acid or S(+)-ibuprofen-D-amino acid may be administered orally, parentarally or topically. The compositions may contain inert carriers such as lactose, starch, calcium sulfate, mannitol and sucrose. Suitable binders, lubricants, flavoring agents, disintegrating agents and coloring agents may also be added.

The increased therapeutic benefits described above for S(+)-ibuprofen-L-amino and S(+)-ibuprofen-D-amino acid can be demonstrated by single oral dose randomized, double-blind studies comparing S(+)-ibuprofen-L-amino acid or S(+)-ibuprofen-D-amino acid to other stereoisomeric forms of ibuprofen and salts thereof in patients experiencing moderate or severe pain following oral surgery. Speed of onset and analgesic efficacy can be evaluated by having patients assess their pain intensity and degree of pain relief at ½, 1, 1½, 2, 3, 4, 5 and 6 hours after dosing. Additionally, patients may use a stopwatch to measure the time until meaningful pain relief was experienced.

Other pain models include postoperative pain, postpartum uterine cramping pain, and dysmenorrhea. The design of all studies is randomized, double-blind and, in addition, the dysmenorrhea studies are a four-menstrual period crossover design. In all studies patients evaluate their degree of pain relief at time points beginning ½ hour after dosing. A stopwatch may be used to measure time to meaningful pain relief. Sample sizes in the studies are sufficient to demonstrate the increased efficacy of S(+)-ibuprofen-L-amino acid or S(+)-ibuprofen-D-amino acid and to detect significant differences in speed of analgesic activity between S(+)-ibuprofen-L-amino acid or S(+)-ibuprofen-D-amino acid and other stereoisomeric forms of ibuprofen and salts thereof.

S(+)-ibuprofen may be prepared following the procedures described in U.S. Pat. No. 4,851,444. Alternatively S(+)-ibuprofen may be prepared following the resolution method given in co-pending U.S. patent application Ser. No. 331,145 filed Mar. 31, 1989, the contents of which are hereby incorporated by reference. L-amino acids and D-amino acids are commercially available from the Sigma Chemical Company or the Aldrich Chemical Company, or S(+)-ibuprofen-L-amino salts and S(+)-ibuprofen-D-amino acid salts may be prepared following the procedure of U.S. Pat. No. 4,279,926 but substituting the particular enantiomers for the racemic mixtures described in that patent.

The following examples illustrate the present invention, its incorporation into pharmaceutical compositions and methods of treatment and as such are not to be considered as limiting the invention set forth in the claims appended hereto.

EXAMPLE 1

Typical Pharmaceutical Compositions Containing a Compound of the Invention

A. Dry Filled Capsules Containing 200 mg of Ibuprofen Per Capsule.

| Ingredient | Amount Per Capsule (mg) |
|---|---|
| S(+)-Ibuprofen-L-Lysine | 342 mg |
| Alcohol SD 3A Anhydrous | — |
| Magnesium Stearate Impalpable Powder NF | 2.00 mg |
| Hard Gelatin Capsule #0 | 96.0 mg |
| | 440 mg |

B. Film Coated Tablet Containing 200 mg of Ibuprofen Per Capsule.

| Ingredient | Amount Per Tablet (mg) |
|---|---|
| S(+)-Ibuprofen-L-Lysine | 342 mg |
| Povidone USP | 17.0 mg |
| Avicel PH102 | 18.0 mg |
| Alcohol SD 3A Anhydrous | — |
| Water Purified | — |
| Magnesium Stearate Impalable Powder NF | 4.00 mg |
| Core Tablet Weight | 381 mg |
| Hydroxypropyl Methylcellulose USP 6CPS | 4.00 mg |
| Hydroxypropyl Cellulose LF NF W/<0.3% Silica | 4.00 mg |
| Titanium Dioxide USP | 1.60 mg |
| Talc USP Purified | 0.40 mg |
| Coated Tablet Weight (Theoretical) Actual Weight (408 mg) Includes the 5% Hydration of Active Ingredient During Granulation | 391 mg |

C: Injectable Solution:

| Ingredient | Amount (mg) |
|---|---|
| S(+)-Ibuprofen-L-lysine* | 27.3 mg |
| Mannitol | 27.3 mg |
| Water for Injection | q.s. to 1.0 ml |

*Equivalent to 16.0 mg of Ibuprofen free acid content.
The above formula may be diluted in Sodium Chloride Injection for slow infusion.

D: Suppository

| Ingredient | Amount (mg) |
|---|---|
| S(+)-Ibuprofen-L-lysine* | 1360 |
| Polyethylene glycol+ | 1631 |
| Tocopherol or BHA or BHT | 9 |

*Equivalent to 800 mg of Ibuprofen free acid content. The drug in this form can be varied from 50 mg to 800 mg Ibuprofen and the necessary glycol or fatty vehicle modified to yield a suppository of about 3 to 3.2 grams.
+A waxy or fatty vehicle such as cocoa butter or Suppocire or Wipepsol can also be employed.

EXAMPLE 2

Preparation of S(+)-Ibuprofen-L-Lysine

A 500 ml 3 neck flask equipped with mechanical stirrer and thermometer was charged with $H_2O$ (42 ml) and L-lysine (37.5 g, 0.25 mole). The mixture was agitated until a solution was obtained. A solution of S(+)-ibuprofen in absolute ethanol (52.6 g, 0.25 mole in 250 ml ethanol) was made up and added to the aqueous lysine over 5 minutes at a temperature $\leq 35°$ C. The resulting solution was filtered through a sintered glass funnel (medium frit) to remove any insoluble material. The filtrate was transferred to a 3000 ml 3-neck flask equipped with a mechanical stirrer, addition funnel and thermometer. To this clear solution was added 575 ml of ethanol over 5 minutes at 20°-25° C. The turbid solution was seeded with the L-lysine salt of S(+)-ibuprofen (50 mg) and an additional 400 ml of ethanol was added over 10 minutes. The resulting suspension was aged at 20°-25° C. for 1 hour with agitation, cooled to 0°-5° C. and held for 1 hour. The product was filtered, washed with 5°±5° C. ethanol (2×1 mmol) and dried in vacuo (50° C.) to yield 74 g (84%) of the titled compound. $[\alpha]_{405} = +14.9°$ C. (C=1, methanol).

EXAMPLE 3

Preparation of S(+)-Ibuprofen-D-Lysine

This compound may be prepared following Example 2 but substituting an equivalent amount of D-Lysine for L-Lysine.

What is claimed is:

1. A compound which is S(+)-ibuprofen-L-amino acid or S(+)-ibuprofen-D-amino acid, substantially free of any other ibuprofen-amino acid stereoisomer.

2. A compound of claim 1 wherein the L-amino acid is selected from L-lysine, L-arginine or L-histidine, and the D-amino acid is selected from D-lysine, D-arginine or d-histidine.

3. A compound of claim 2 wherein the L-amino acid is L-lysine and the D-amino acid is D-lysine.

4. A compound of claim 3 which is S(+)-ibuprofen-L-lysine.

5. A compound of claim 2 wherein the L-amino acid is L-arginine and the D-amino acid is D-arginine.

6. A compound of claim 1 wherein the weight ratio of S(+)-ibuprofen-L-amino acid or S(+)-ibuprofen-D-amino acid to other stereoisomers of this salt is at least 95:5.

7. A compound of claim 6 wherein the weight ratio of S(+)-ibuprofen-L-amino acid or S(+)-ibuprofen-D-amino acid to other stereoisomers of this salt is at least 99:1.

8. A compound of claim 7 wherein the L-amino acid is L-lysine and the D-amino acid is D-lysine.

9. A compound of claim 8 which is S(+)-ibuprofen-L-lysine.

10. A compound of claim 7 wherein the L-amino acid is L-arginine, and the D-amino acid is D-arginine.

11. A pharmaceutical composition useful in the treatment of pain and inflammation which comprises a pharmaceutically acceptable carrier and a pharmaceutically effective amount of a compound of claim 1.

12. A composition of claim 11 wherein the pharmaceutically effective compound is S(+)-ibuprofen-L-lysine, or S(+)-ibuprofen-D-lysine.

13. A composition of claim 12 wherein the pharmaceutically effective compound is S(+)-ibuprofen-L-lysine.

14. A pharmaceutical composition for eliciting an onset-hastened, enhanced analgesic response in a human organism in need of such treatment, said composition comprising an onset-hastening, enhancing analgesically, effective amount of S(+)-ibuprofen-L-amino acid or S(+)-ibuprofen-D-amino acid substantially free of any other ibuprofen-amino acid stereoisomer, and a nontoxic pharmaceutically acceptable carrier.

15. A composition of claim 14 in which the L-amino acid is L-lysine, and the D-amino acid is D-lysine.

16. A composition of claim 15 in which the pharmaceutically effective compound is S(+)-ibuprofen-L-lysine.

17. A composition of claim 14 in which the L-amino acid is L-arginine, and the D-amino acid is D-arginine.

18. A method of treating pain and inflammation in a human subject in need of such treatment, comprising administering to such organism an onset-hastening, enhancing analgesically, effective amount of S(+)-ibuprofen-L-amino acid or S(+)-ibuprofen-D-amino acid substantially free of any other ibuprofen amino acid steroisomer.

19. A method of claim 18 wherein the L-amino acid is L-Lysine, and the D-amino acid is D-lysine.

20. A method of claim 19 wherein the effective compound is S(+)-ibuprofen-L-lysine.

21. A method of claim 18 wherein the L-amino acid is L-arginine, and the D-amino acid is D-arginine.

22. A method of claim 18 in which the amount of S(+)-ibuprofen-L-amino acid or S(+)-ibuprofen-D-amino acid administered is 50 mg to 600 mg measured in mg ibuprofen.

23. A method of claim 22 in which the amount administered is 50 to 300 mg measured in mg ibuprofen.

* * * * *